(12) United States Patent
Olson

(10) Patent No.: US 10,507,133 B2
(45) Date of Patent: Dec. 17, 2019

(54) INJECTABLE SECUREMENT DEVICE AND RELATED DELIVERY SYSTEM AND METHOD OF USE

(71) Applicant: The Regents of the University of Colorado, a body corporate, Denver, CO (US)

(72) Inventor: Jeffrey Olson, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 1063 days.

(21) Appl. No.: 14/332,475

(22) Filed: Jul. 16, 2014

(65) Prior Publication Data

US 2015/0025540 A1     Jan. 22, 2015

Related U.S. Application Data

(60) Provisional application No. 61/846,770, filed on Jul. 16, 2013.

(51) Int. Cl.
*A61F 2/16* (2006.01)
*A61F 9/00* (2006.01)
*A61B 17/04* (2006.01)

(52) U.S. Cl.
CPC .... *A61F 9/0017* (2013.01); *A61B 2017/0406* (2013.01); *A61F 2210/0004* (2013.01); *A61F 2210/0014* (2013.01); *A61F 2220/0016* (2013.01)

(58) Field of Classification Search
CPC ........ A61B 17/0401; A61B 2017/0404; A61B 2017/0406; A61B 2017/0464; A61B 17/0487; A61B 2017/0409; A61B 2017/0414; A61F 9/0017
USPC ................................................ 606/213, 232
See application file for complete search history.

(56) References Cited

U.S. PATENT DOCUMENTS

| | | | | |
|---|---|---|---|---|
| 2005/0125031 | A1* | 6/2005 | Pipenhagen | A61B 17/0057 606/213 |
| 2006/0190041 | A1* | 8/2006 | Fallin | A61B 17/0401 606/232 |
| 2007/0185532 | A1* | 8/2007 | Stone | A61B 17/0401 606/232 |
| 2011/0301638 | A1* | 12/2011 | Walters | A61B 17/0057 606/213 |

* cited by examiner

Primary Examiner — Melanie R Tyson
(74) Attorney, Agent, or Firm — Snell & Wilmer L.L.C.

(57) ABSTRACT

An injectable securement device includes one or more sutures and a bolster housed inside an elongate element, and may be part of a system that also includes one or more fastening elements and an elongate element. Injecting a suture tie/knot can be accomplished outside the eye without the need for performing the action of tying within the eye.

5 Claims, 14 Drawing Sheets

INJECTABLE SECUREMENT DEVICE AND RELATED DELIVERY SYSTEM AND METHOD OF USE

CROSS-REFERENCE TO RELATED APPLICATION

This application claims priority to U.S. Provisional Patent Application Ser. No. 61/846,770 filed on Jul. 16, 2013 and entitled "Injectable Securement Device and Related Delivery System and Method of Use," which is incorporated herein by reference in its entirety.

BACKGROUND

Field

The present disclosure generally relates to securing tissue and implantable materials for use in surgical and microsurgical settings.

Discussion of the Related Art

Numerous suturing and securing devices and surgical manipulations exist for both surgical and microsurgical settings, Intraocular objects need to be secured, as do tissue, implants, and drug delivery mechanisms. Securing such objects presents challenges due to both space and time constraints. Once secured, dislocation of such objects is undesirable, yet prevalent. Space constraints make suturing inside the eye a technically challenging endeavor, and can result in a skilled surgeon 20 times longer to perform than conventional suturing. There is thus a need for an injectable securement device and related delivery system and method of use. The present disclosure addresses this need.

SUMMARY

An injectable securement device according to example embodiments of the present disclosure comprises a suture forming a hitch through a bolster, wherein the suture includes a fastening element at an end, and wherein applying tension to the end cinches a loop of the hitch against the bolster to secure an object.

A system for securing an intraocular object according to example embodiments of the present disclosure comprises an injectable securement device comprising a suture forming a hitch through a bolster, wherein the suture includes a fastening element at an end, and wherein applying tension to the end cinches a loop of the hitch against the bolster to secure an object. A system according to example embodiments of the present disclosure further comprises an elongate element having a lumen extending therethrough and being configured to pierce tissue with a distal end, wherein the suture is threaded through the elongate element, and wherein the injectable securement device is configured to be deployed from the distal end.

A method of securing an intraocular object according to example embodiments of the present disclosure comprises (i) piercing an external sclera with an elongate element; (ii) inserting the elongate through the external sclera such that a distal end of the elongate element is located in an anterior chamber of an eye; (iii) deploying an injectable securement device from the distal end into the anterior chamber, wherein the injectable securement device comprising a suture forming a hitch through a bolster; (v) manipulating a loop of the hitch around an intraocular object; (v) pulling a proximal end of the suture to cinch the loop against the bolster; (v) removing the elongate element; and (vii) securing the suture to the external sclera.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

DETAILED DESCRIPTION OF THE ILLUSTRATIVE EMBODIMENTS

Figure 1:
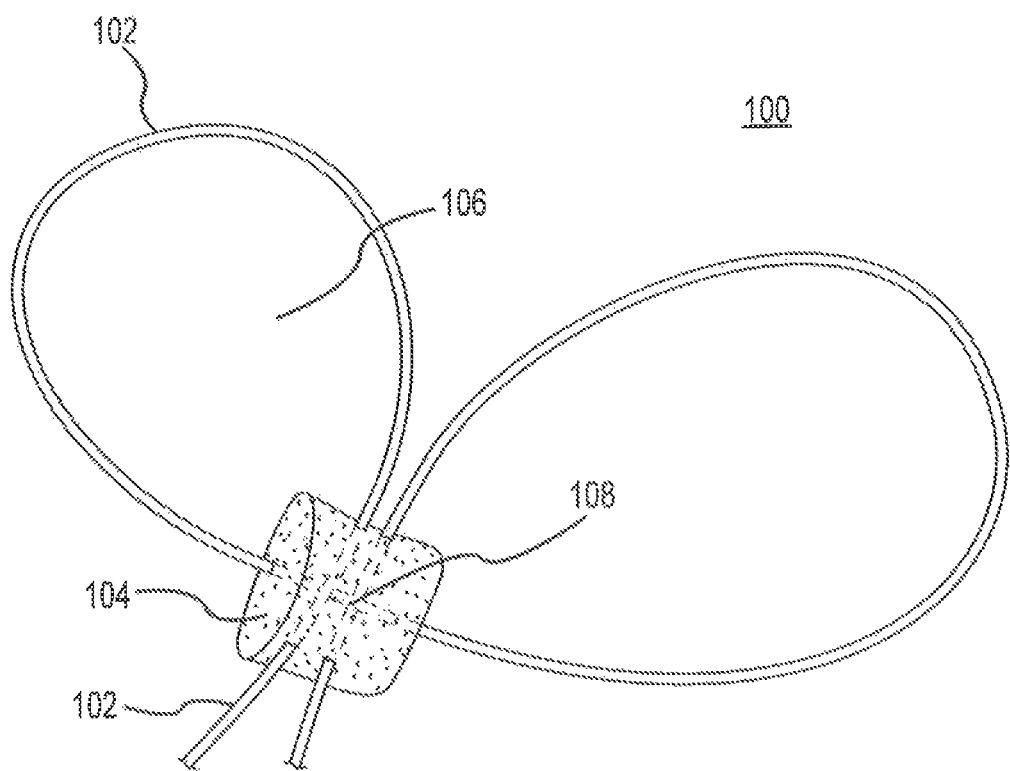
FIG. 1 illustrates an injectable securement device in accordance with the present disclosure.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "proximal" and "distal," when used herein in relation to a device or device component, refer respectively, to directions closer to and farther away from the device's operator.

The present disclosure generally relates to securing intraocular objects. An injectable securement device and related delivery system and method of use is disclosed herein.

The injectable securement device of the present disclosure can be particularly useful in ophthalmic surgeries and procedures including securement in iris defects, securing or fixing in place intraocular implants such as intraocular lenses, glaucoma tube shunts, implantable hardware for the eye, securing full and partial thickness cornea transplants, LASIK and DSEK/DLEK flaps, temporary and permanent keratoprostheses, implantable ocular lenses, contact lenses and telescopic lenses, presbyopia reversal, scleral patch grafts and scleral rings, conjunctival and amniotic membrane grafts, repair of the iris and isis root defects, iridoplasty, pupiloplasty, securing dislocated intraocular lenses to the iris, anchoring the capsular bag, anchoring capsular tension rings, corneal wound closure, anchoring tube shunts both in the anterior chamber and externally to the sclera, closure of sclerotomies, conjunctival flaps, trabeculotomy and trabeculectomy blebs, closure of cyclodialysis clefts, fixation of intraocular pressure monitoring devices, fixation of intraocular implants for sustained drug delivery, anchoring orbital reconstruction hardware, weighted lid implants, eyelid skin and muscle wound closure, fixation of lacrimal system hardware, tarsorraphy, repair of ptosis, blepharoplasty, correction of entropion and ectropion, canthoplasty, fixation of virectomy infusion line, closure of sclerotomies, scleral buckling with or without silicone band or sponge hardware, retinopexy, closure of traumatic corneal and scleral wounds, fixation of radioactive plaques for the treatment of intraocular tumors, fixation of intraocular hardware and implantable chips for artificial vision and electrical stimulation of the retina, correction of blepharospasm, and fixation of extraocular muscles to sclera for resection, recession, and transposition surgeries.

With reference now to FIG. 1, an injectable securement device 100 in accordance with the present disclosure comprises one or more sutures 102 and a bolster 104. Suture 102 is generally an elongate, flexible element configured to form one or more of a loop 106 and be tied into a securement 108. Suture 102 can be comprised of various materials, for example those that are biocompatible, such as nylon, polypropylene, wire, a metal, an alloy, a shape-memory material (e.g., nitinol or a shape-memory polymer) or the like. Other materials include, but are not limited to, catgut, chromic catgut, nylon, polypropylene, polyglycolide, polydiaoxanone, vicryl, mersilene, various plastics, polymers, threads, single filament, monofilament. Suture 102 can be comprised of a dissolvable material. Suture 102 can be coated with a therapeutic agent.

Bolster 104 is generally a structure configured to prevent unraveling of loop 106 and/or slipping of securement 108, whether before and/or after intraocular deployment of injectable securement device 100. Bolster 104 can be a material that is soft or elastic, or otherwise into which suture 102 can be pressed and around which suture 102 can be cinched. Bolster 104 can be comprised of various materials, for example those that are biocompatible, such as silicone, PMA, or other polymers, acrylics or the like. Other materials include, but are not limited to, hydroxyapatite, PVDF, collamer, collagen, shape memory, plastics, polymers. Bolster 104 can be comprised of a dissolvable material. Bolster 104 can be imbibed with a therapeutic agent.

In accordance with an example injectable securement device 100 of the present disclosure, suture 102 is threaded through bolster 104 to form one or more of loop 106 and be tied into securement 108. Securement 108 can be a hitch (e.g., a cow or clove hitch), a surgeon's knot, a cinch knot, another suitable knot, a bend, or the like. In this manner, bolster 104 prevents unraveling of loop 106 and/or slipping of securement 108. Bolster 104 and suture 102 can be housed inside the lumen of an elongate element, and deployed once inside the eye.

Figure 2:
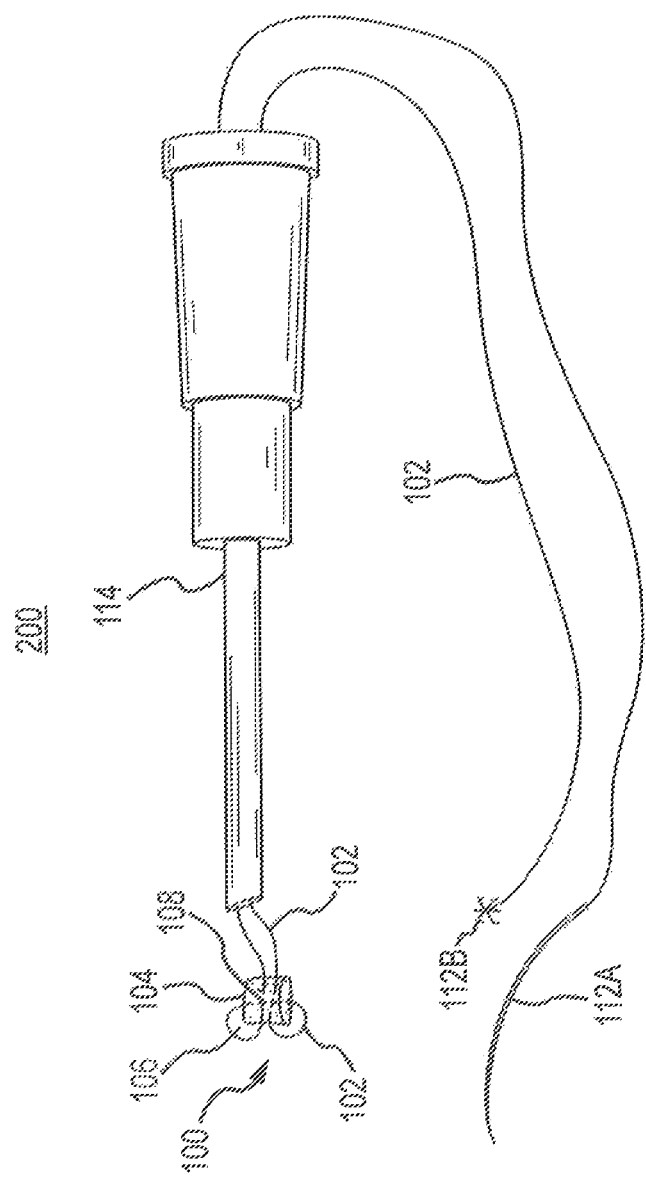
FIG. 2 illustrates a system in accordance with the present disclosure.

With reference to FIG. 2, a system 200 in accordance with the present disclosure comprises injectable securement device 100 as described above, one or more fastening elements, and an elongate element 114. A fastening element as described herein is generally configured to be coupled with an end of suture 102 as described above, puncture tissue, and/or secure suture 102 with respect to the tissue, for example, on a tissue inner surface, a tissue outer surface, and/or through the tissue as with suturing techniques known in the art. In various embodiments, a fastening element comprises a needle 112A (e.g., to tie suture 102) or an anchor 112B. In some embodiments anchor 112B pierces the tissue, while in other embodiments anchor 112B does not pierce the tissue. Suture 102 can have the same or different fastening elements on its proximal ends.

Elongate element 114 as described herein is generally any longitudinally extending structure configured to have a lumen extending therethrough, through which injectable securement device 100 as described above, and one or more fastening element can be passed. Thus, elongate elements include but are not limited to cannulas, trocars, needles, ports, introducer sheaths, introducers, sheaths, tubes with lumens (e.g., catheters), hollow wires (e.g., guidewires), hollow stylets, metal tubes (e.g., hypotubes), and polymer tubes. Elongate elements can be any material and can have any cross-sectional shape including, but not limited to, profiles that are elliptical (e.g., circles, ovals, ellipses, and the like), non-elliptical (e.g., triangles, rectangles, squares, hexagons, trapezoids, pentagons, stars, and the like), or random. Moreover, the cross-section can vary in shape and/or size from end to end. Elongate element 114 can be further configured at its distal end to pierce or puncture tissue, for example, by having an angled or sharpened end.

In example embodiments, suture 102 extends into a proximal end of elongate element 114, through a distal end of elongate element 114, and to bolster 104 where securement 108 is formed. In example embodiments, the same suture 102 extends from bolster 104, back on itself through the distal end of elongate element 114, and out the proximal end of elongate element 114. In other example embodiments, a second suture 102 extends from bolster 104, back on the first suture 102 through the distal end of elongate element 114, and out the proximal end of elongate element 114.

In yet other example embodiments, no suture 102 extends from bolster 104 back through the distal end of elongate element 114 and out the proximal end of elongate element 114. In such embodiments, a loop, slip knot, noose or the like can be used at the distal end of suture 102 to form loop 106.

System 200 in accordance with example embodiments of the present disclosure can have a small crossing profile, for example less than about 25 gauge, about 16 gauge, or smaller. Elongate element 114 can thus have a small crossing profile in accordance with example embodiments of the present disclosure, for example less than about 25 gauge, about 16 gauge, or smaller.

System 200 in accordance with example embodiments of the present disclosure can comprise a plurality of injectable securement devices 100 of the present disclosure. Such plurality of injectable securement devices 100 can be deployed adjacent to one another in a simultaneous manner. Alternatively, such plurality of injectable securement devices 100 can be deployed in an sequential manner.

Figure 3:
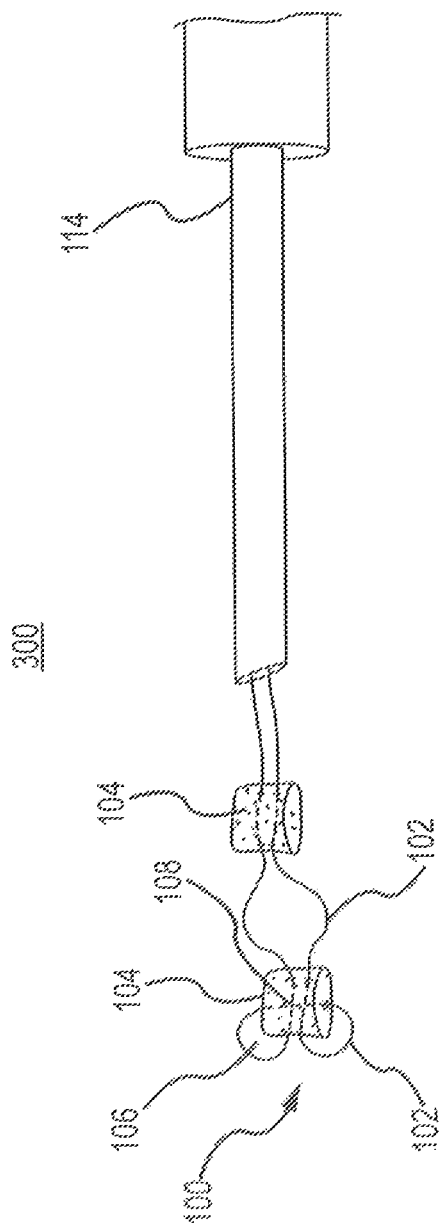
FIG. 3 illustrates a system comprising a plurality of bolsters in accordance with the present disclosure.

With reference to FIG. 3, disclosed is a system 300 comprising a plurality of bolsters 104. In such embodiments, suture 102 can comprise slack between the plurality of bolsters 104 to provide for adjustment. For instance, one side of suture 102 can be pulled more than the other side of suture 102. A strut can also be used between a plurality of bolsters 104 such that the strut acts as a spacer, to prevent the bolsters from touching while allowing slack to be generated or removed in suture 102.

A method of use is also disclosed herein. In example embodiments, injecting a suture tie/knot can be accomplished outside the eye without the need for performing the action of tying within the eye. By way of illustration only, one or more loops 106 may be formed ex vivo with respect to one or more bolsters 104. Such loop(s) 106 can be inserted into the eye from the end of elongate element 114 and manipulated around an intraocular object to be grasped. Such loop(s) 106 can then be cinched closed against bolster(s) 104 by applying tension to one or more sutures 102 forming such loop(s) 106. In this manner, the intraocular object can be grasped without the need for performing the action of tying in vivo.

In general, while the present disclosure will be described primarily with reference to securing intraocular objects, and intraocular lenses, it will be apparent to those skilled in the art that the disclosure can be applied to securing any objects. whether in surgical or non-surgical settings.

Figure 4A:
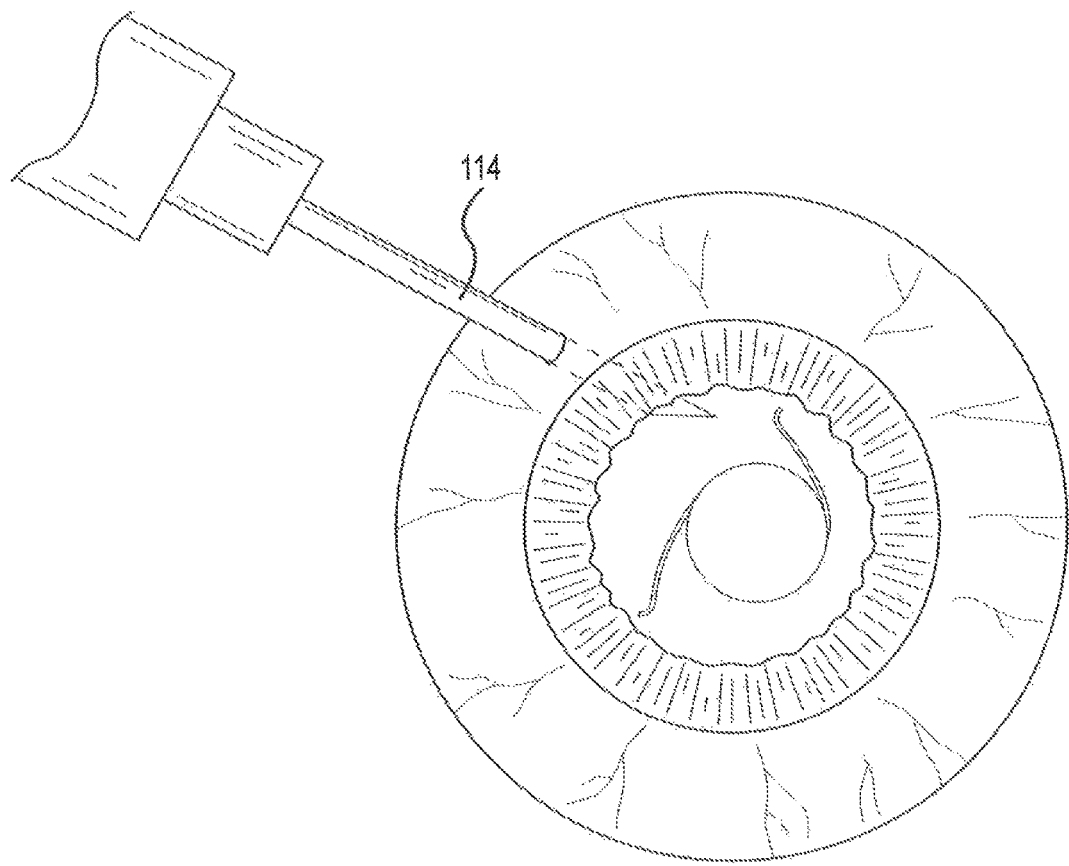
FIGS. 4A-4F progressively illustrate a method of use in accordance with the present disclosure.

That said, and as an illustrative example only with reference to FIGS. 4A-4F, a method of use of system 200 as described above comprises performing a sclerotomy and passing the distal end of elongate element 114 therethrough, into the anterior chamber (see FIG. 4A).

Injectable securement device 100 can then be deployed via pars plana from the distal end of elongate element 114 (see FIG. 4B), into the anterior chamber. Injectable securement device 100 can be pushed out of, or pulled out from, the distal end of elongate element 114. To accomplish the former, suture 102 having a relatively high column strength, or a rod, plunger or the like, can be used. In yet other embodiments, injectable securement device 100 can be pushed out of the distal end of elongate element 114 with a gas (e.g., air or octafluoropropane), fluid (e.g., balanced salt solution), or viscoelastic material.

Figure 4B:
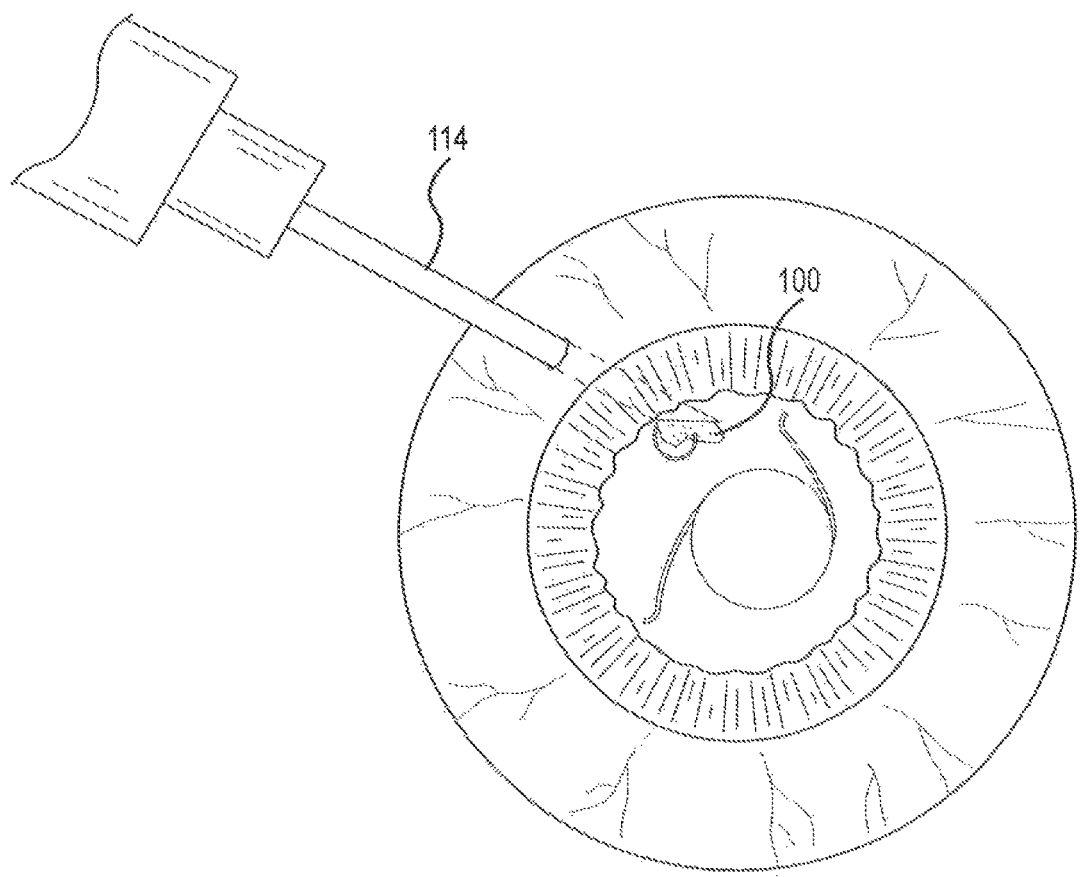
Figures 1, 4B:
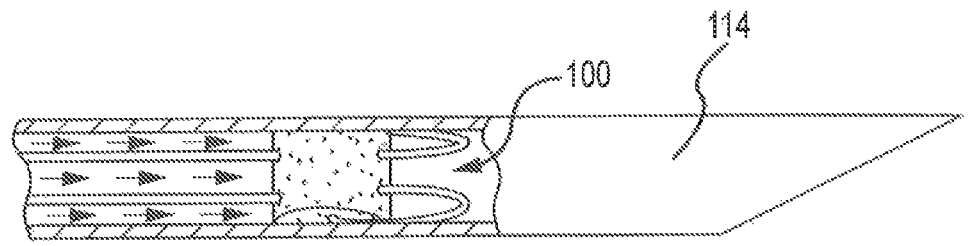
Figures 2, 4B:
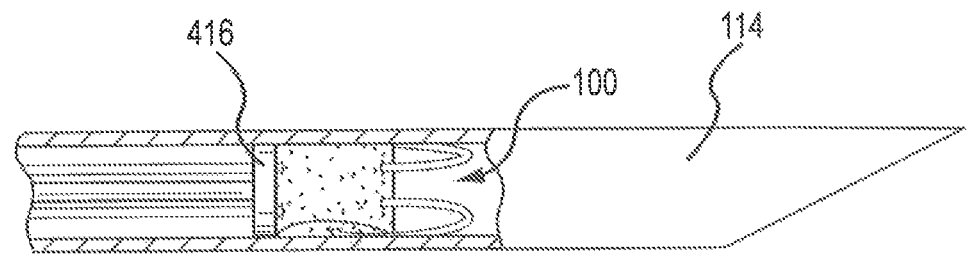

For example, and with reference to FIG. 4B-1, pressure in the form of a gas, fluid, or viscoelastic material can be used to advance injectable securement device 100 out the distal end of elongate element 114.

With reference to FIG. 4B-2, as noted above, a rod or plunger 416 can be used to advance injectable securement device 100 out the distal end of elongate element 114.

A deployment device of the present disclosure for delivering and securing injectable securement device 100 at a surgical site includes a hollow housing having a first end and a second end, a hollow deployment chamber or body positioned within, and/or extending from, the first end of the hollow housing, and an actuator mechanism positioned within, and/or extending from, the second end of the hollow housing. In one illustrative embodiment, the hollow housing and the hollow deployment chamber may both be cylindrical in shape or have a "tube" shape. One or more injectable securement devices 100 are loaded into the hollow deployment chamber before utilizing the deployment device to deliver and secure injectable securement device 100. In one illustrative embodiment, the hollow deployment chamber is configured to anchor injectable securement device 100 or clip within the deployment device, for example, by frictional engagement.

In one illustrative embodiment, the actuator mechanism is configured to anchor a distal end of injectable securement device 100, for example, by frictional engagement, mechanical engagement, adhesion, etc. In this manner, the actuator mechanism may be configured to deploy injectable securement device 100 from the deployment device once injectable securement device 100 is in a desired position. Similarly, the actuator mechanism may be configured to retract injectable securement device 100 so that it may be repositioned if necessary.

In another illustrative embodiment, the actuator mechanism includes an actuator rod contained within the second end of the hollow housing and an ejector pin contained within, and/or extending from, the actuator rod that is capable of fitting within the hollow deployment chamber. The proximal end of the ejector pin may be completely contained within the hollow deployment chamber at all times and the hollow deployment chamber may have a sharpened proximal end for piercing tissue to allow access to a deployment site.

In another illustrative embodiment, the deployment device of the present disclosure may also include one or more finger supports attached to an outer surface of the hollow housing for supporting a user's fingers while employing the actuator mechanism of the deployment device in order to allow for greater control while utilizing the deployment device. The finger support may include a single opening or two openings on opposite sides of the hollow housing for inserting a user's finger(s) therethrough.

In yet another illustrative embodiment, the deployment device of the present disclosure may include a thumb support attached to the actuator mechanism for supporting a user's thumb while employing the actuator mechanism. The thumb support may comprise a post or include an opening for inserting a user's thumb therethrough.

In still another illustrative embodiment, the actuator mechanism may include a geared or ratcheted system that deploys injectable securement device 100 by either rotation of the deployment chamber or compression of a button or lever or a system that deploys injectable securement device 100 by twisting, wheeled action or sliding. Alternatively, in yet another illustrative embodiment, the actuator mechanism may comprise a pneumatically driven system or a hydraulically driven system such as those currently known in the art. In yet another illustrative embodiment, the actuator mechanism of the present disclosure may be capable of interfacing with a foot pedal or a trigger device configured to control deployment of injectable securement device 100.

In another illustrative embodiment of the deployment device, the deployment device may include a mechanism capable of retracting injectable securement device 100 from the body. In yet another illustrative embodiment, the actuator mechanism of the present disclosure can be a viscoelastic that deploys injectable securement device 100.

In yet another illustrative embodiment, the deployment device of the present disclosure may be capable of interfacing with a robotic arm for remote or telescopic surgery, but could be semisolid, viscous, pneumatic, or hydraulic in nature.

Figure 4C:
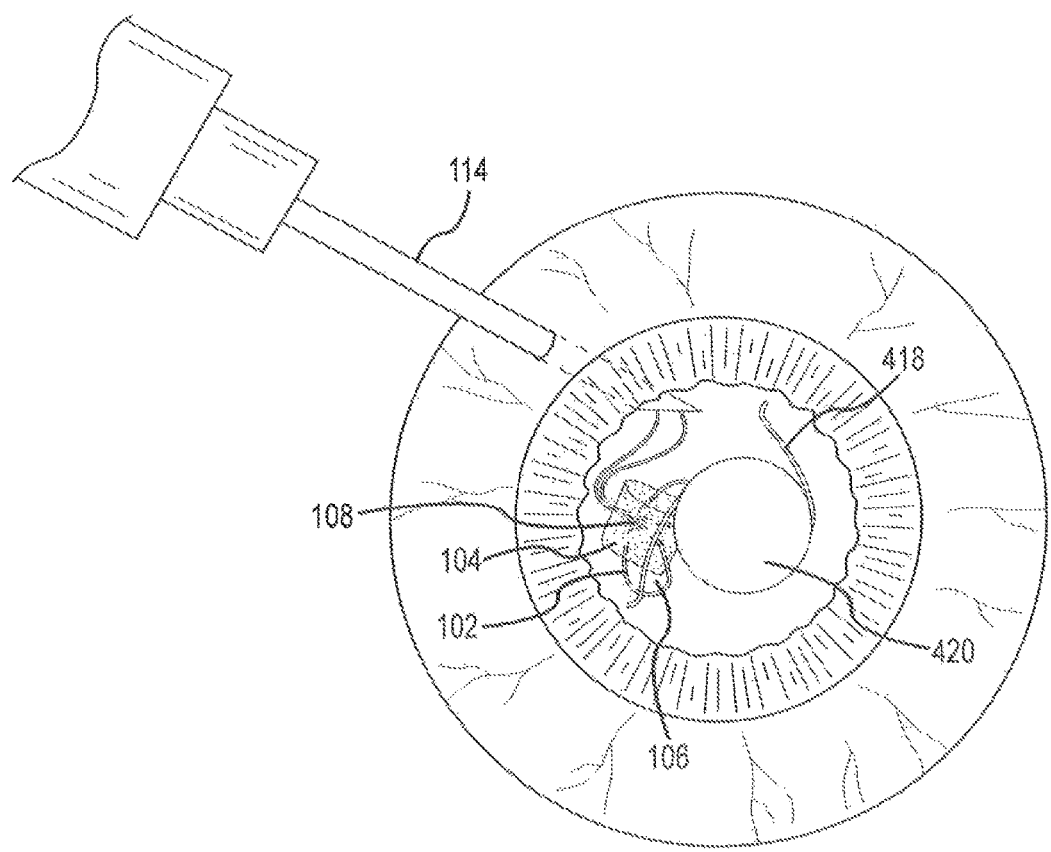
Figure 4D:
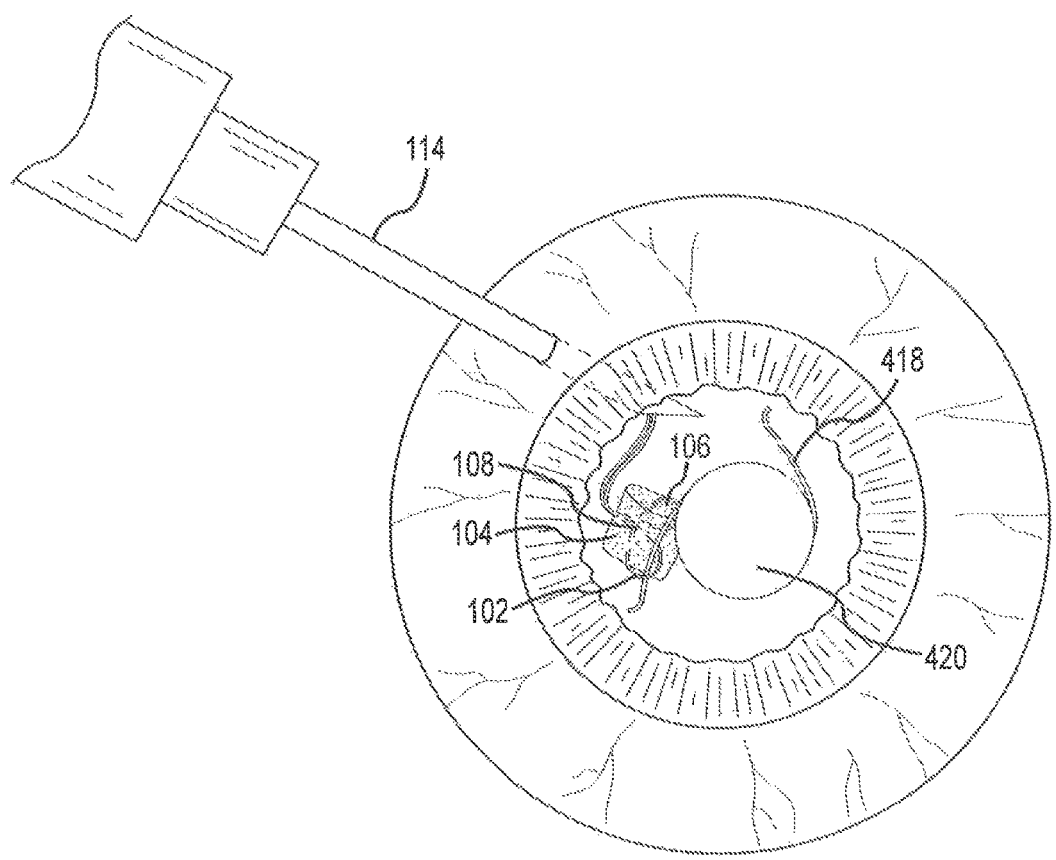
Figure 4E:
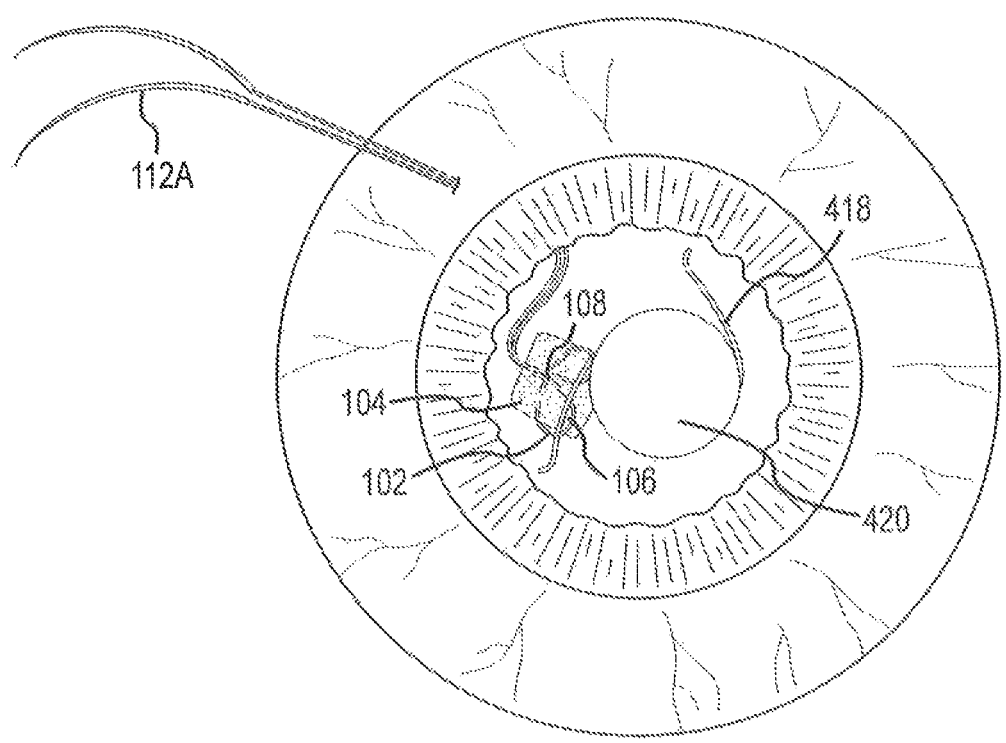
Figure 4F:
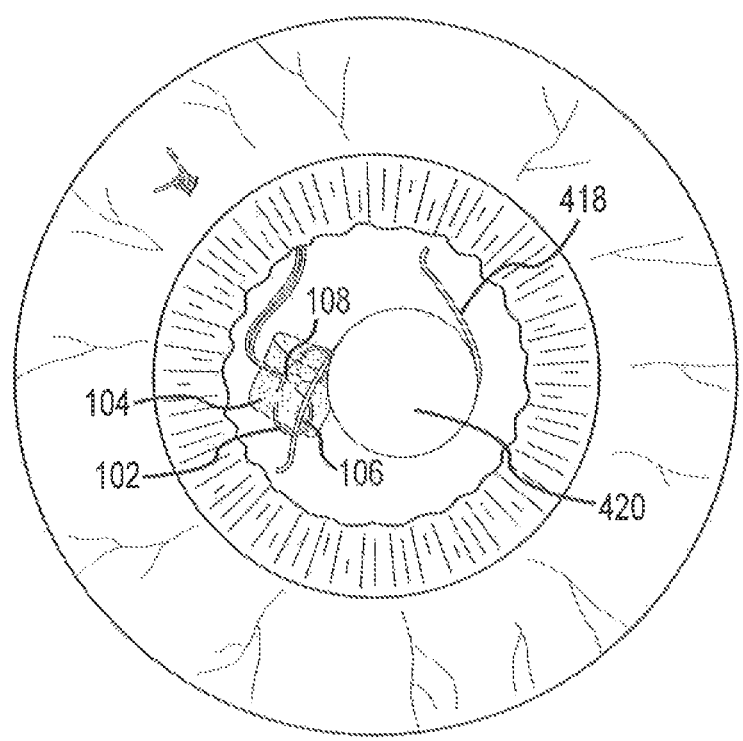

An intraocular object to be secured (or a portion thereof, e.g., a haptic 418 of an intraocular lens 420) can then be captured by passing it completely or partially through loop 106 of injectable securement device 100 (see FIG. 4C). Tension can then be applied to the proximal end of suture 102 to cinch securement 108 of injectable securement device 100, and thereby secure the intraocular object against bolster 104 (see FIG. 4D). Bolster 104 can remain in vivo to prevent slipping of securement 108, or can be comprised of a dissolvable material. In other embodiments, bolster 104 can be removed.

Elongate element 114 can then be removed over injectable securement device 100 and the fastening element(s). The fastening element can then be deployed and used to dose the sclerotomy and secure suture 102 to the external sclera. For example, needle 112A can be deployed upon removal of elongate element 114 (see FIG. 4E) and used to dose the sclerotomy and secure suture 102 to the external sclera (see FIG. 4F) using suturing techniques known in the art.

Such a method of use can decrease the time and difficulty associated with prior art approaches. For example, such a method of use can be at least about twenty times faster than prior art approaches (1 min vs. 20 min).

In various embodiments, securing a haptic of an intraocular lens to the external sclera as described above (versus securing it within the anterior chamber) also provides for minimally invasive adjustability. As an example, tension can be applied to suture 102 to adjust the location of the intraocular lens without the need for a further sclerotomy.

Figure 5A:
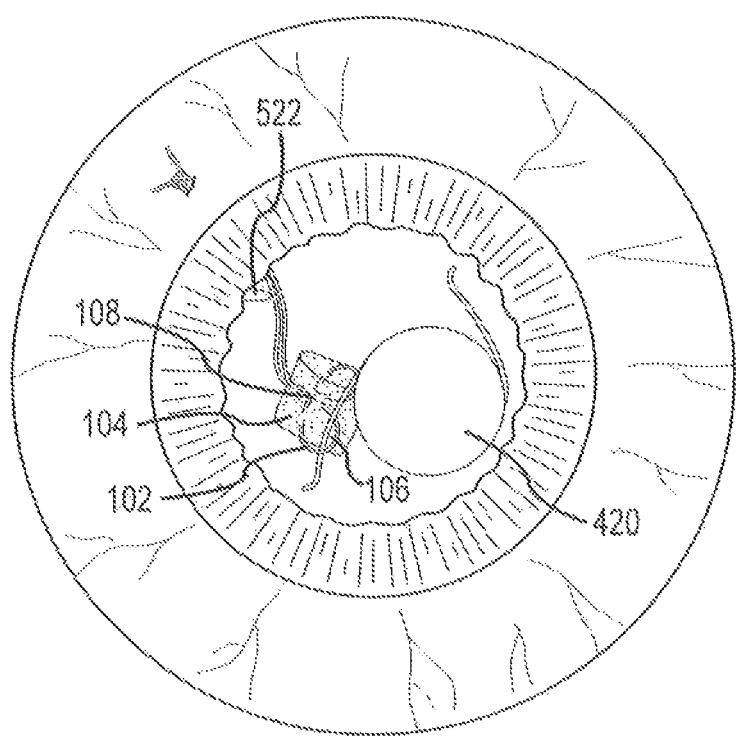
FIGS. 5A-5B illustrate a system comprising a pulley system for adjustability in accordance with the present disclosure.
Figure 5B:
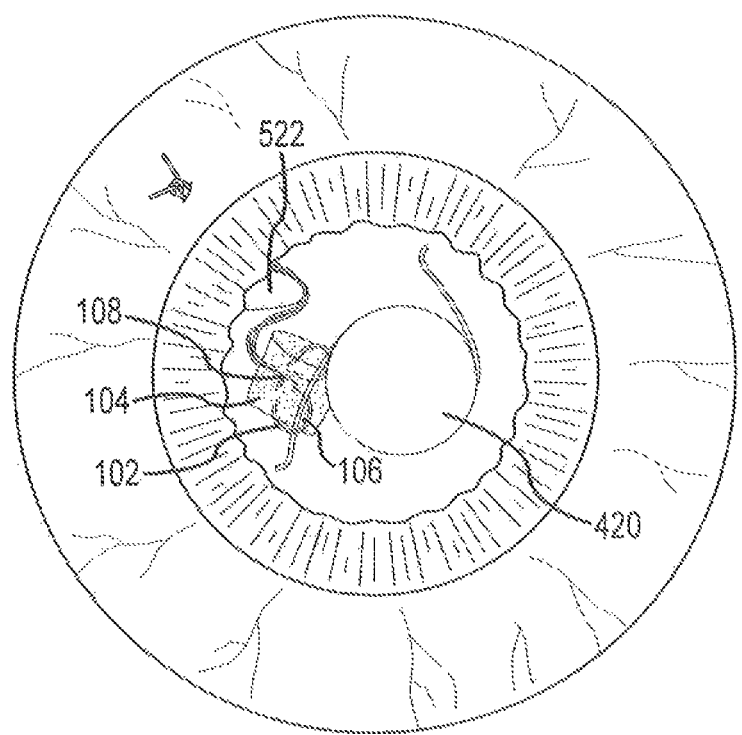

Tension can be applied to suture 102, in a pulley-type manner. By way of example, and with reference to FIGS. 5A-5B, disclosed is a system comprising a pulley system for adjustability. Such a system comprises a fulcrum 522. Fulcrum 522 can be configured to expand and/or contract, and upon said expansion or contraction, cause tension on suture 102, thereby moving intraocular lens 420. Such movement can be in the lateral, anterior and/or posterior direction, thereby facilitating centration and/or focal length adjustability for intraocular lens 420.

Fulcrum 522 can be configured to expand and/or contract in response to osmotic swelling, heating, cooling, twisting, a shape-memory material, an elastic material, etc. Fulcrum 522 can be attached directly or indirectly to a tissue within an eye, for example, an internal wall of an anterior chamber.

An adjustable system for variable and dynamic tension on suture 102 as described herein, can be used, among other applications, for movement of an intraocular lens for an accommodating lens or reversal of presbyopia.

Figure 6A:
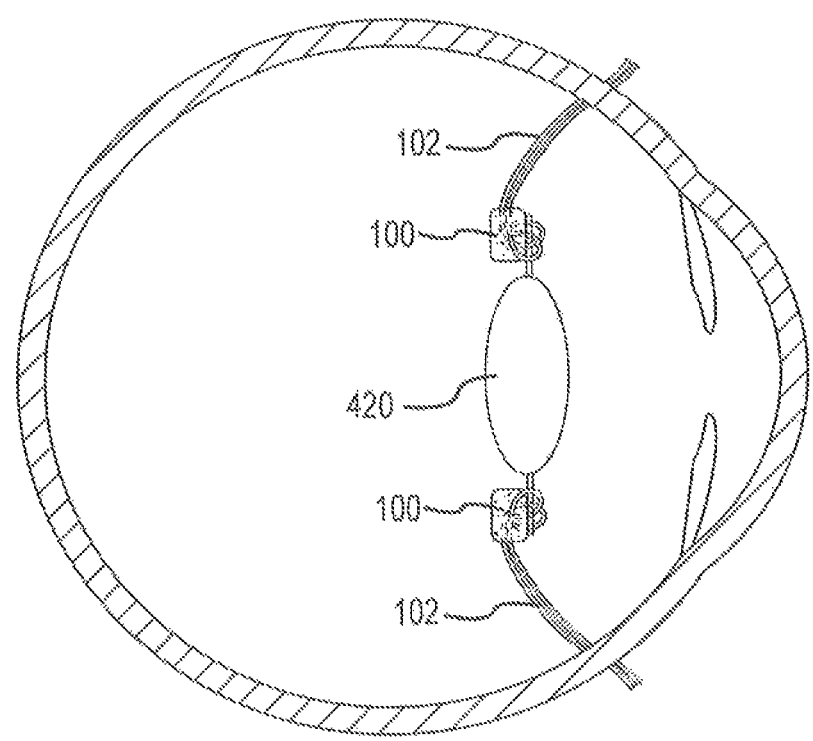
FIGS. 6A-6B illustrate an intraocular lens secured with a plurality of injectable securement devices in accordance with the present disclosure.
Figure 6B:
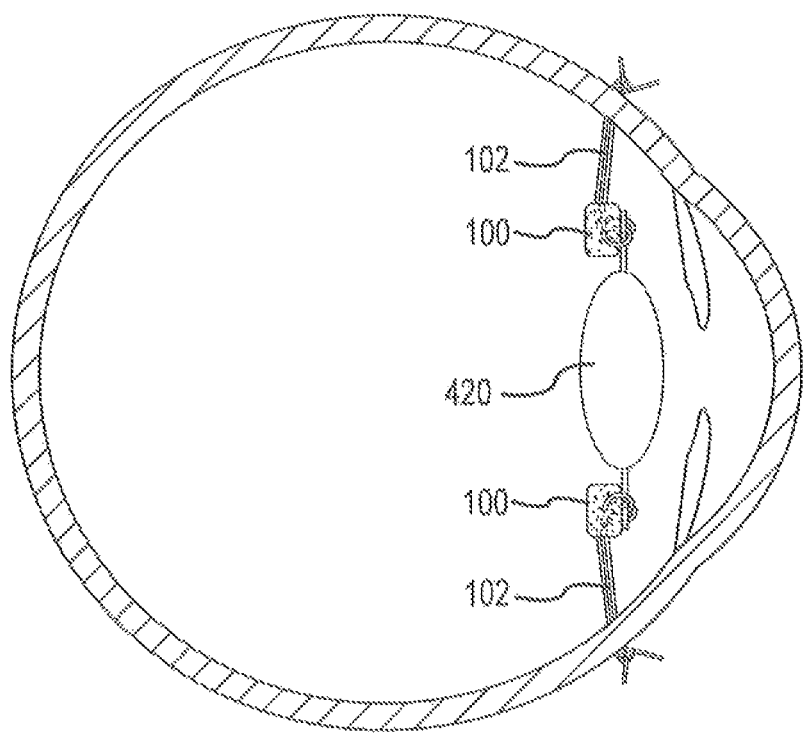

With reference to FIG. 6, disclosed is an intraocular lens 420 secured with a plurality of injectable securement devices 100. While two injectable securement devices 100 are illustrated for simplicity, it will be apparent to those skilled in the art that three, four, five, six or more injectable securement devices 100 can be used in connection with the present disclosure, in such embodiments, applying tension to suture 102 can move or adjust intraocular lens 420. Such movement can be in the lateral, anterior and/or posterior direction, thereby facilitating centration and/or focal length adjustability for intraocular lens 420. Applying tension to suture 102 can be done prior to being secured to the external sclera during an initial procedure, Notwithstanding the foregoing, applying tension to suture 102 can also be done in a later procedure. Each suture 102 can be attached to one or more of the remaining sutures 102 at a location where such sutures 102 are secured to the external sclera. In other embodiments, each suture 102 can be attached to one or more of the remaining sutures 102 wherein none of such attached sutures 102 are secured to the external sclera.

Yet other intraocular applications include presbyopia reversal optical systems, pupilloplasty procedures, glaucoma drainage devices, scleral buckles, etc.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

I claim:

1. A system for grasping an intraocular object comprising:
an injectable securement device comprising a suture forming a securement through and around a bolster, wherein applying tension to the suture cinches a closed loop of the securement against the bolster to grasp an intraocular object extending through the loop and secure the intraocular object against the bolster, wherein the bolster is comprised of a material that is resiliently deformable such that the suture deforms the bolster when the suture is pulled tight around the bolster to prevent unraveling of the loop and slipping of the securement, and further wherein the suture is threaded through the bolster along two different axes of the bolster; and
an elongate element having a lumen extending therethrough, the elongate element comprising an actuator mechanism, and the elongate member being configured to pierce tissue with a distal end, wherein the suture is threaded through the elongate element, and wherein the injectable securement device is configured to be deployed from the distal end by the actuator mechanism.

2. The system of claim 1, wherein the elongate element is a cannula.

3. The system of claim 1, wherein the bolster is comprised of a dissolvable material.

4. The system of claim 1, wherein the actuator mechanism is at least one of pneumatically driven and hydraulically driven, wherein the injectable securement device is frictionally anchored within the lumen so as to be deployed from the distal end by pressure in the form of a gas, fluid, or viscoelastic material.

5. The system of claim 1, wherein the actuator mechanism comprises at least one of a rod and a plunger, wherein the injectable securement device is configured to be deployed from the distal end using the rod or the plunger.

* * * * *